United States Patent [19]

Smith

[11] Patent Number: 5,900,249
[45] Date of Patent: May 4, 1999

[54] MULTICOMPONENT PAIN RELIEF TOPICAL MEDICATION

[76] Inventor: David J. Smith, 8851 Center Dr., Suite 412, La Mesa, Calif. 91942

[21] Appl. No.: 09/021,035

[22] Filed: Feb. 9, 1998

[51] Int. Cl.$^6$ .............................. A61F 13/00; A61L 15/16
[52] U.S. Cl. ............................................ 424/443; 424/447
[58] Field of Search ................................... 424/447, 448, 424/449, 443

[56] References Cited

U.S. PATENT DOCUMENTS

| | | | |
|---|---|---|---|
| 4,360,518 | 11/1982 | Rovee et al. | 424/240 |
| 4,440,777 | 4/1984 | Zupan | 424/274 |
| 4,473,565 | 9/1984 | Rovee et al. | 424/241 |
| 4,752,612 | 6/1988 | Saito et al. | 514/420 |
| 4,767,751 | 8/1988 | Davis | 514/179 |
| 4,783,450 | 11/1988 | Fawzi et al. | 514/78 |
| 4,879,119 | 11/1989 | Konno et al. | 424/449 |
| 4,940,701 | 7/1990 | Davis | 514/179 |
| 4,954,487 | 9/1990 | Cooper et al. | 514/159 |
| 4,970,206 | 11/1990 | Alexander et al. | 514/174 |
| 5,066,648 | 11/1991 | Alexander et al. | 514/174 |
| 5,153,179 | 10/1992 | Eibl | 514/34 |
| 5,290,561 | 3/1994 | Farhadieh et al. | 424/449 |
| 5,352,456 | 10/1994 | Fallon et al. | 424/448 |
| 5,372,819 | 12/1994 | Godbey et al. | 424/449 |
| 5,399,355 | 3/1995 | Riedl et al. | 424/449 |
| 5,422,118 | 6/1995 | Brown et al. | 424/449 |
| 5,460,821 | 10/1995 | Masiz | 424/448 |
| 5,474,783 | 12/1995 | Miranda et al. | 514/14 |
| 5,612,382 | 3/1997 | Fike | 514/14 |

OTHER PUBLICATIONS

Ballerini, R., et al., J. of Clinical. Pharmacolog. Research, *Absorption Rate of Ketoprofen Topically Administered in Man*; VI:69–72 (1986) (Abstract Only).

Chi, S., et al., *Release Rates of Ketoprofen from Poloxamer Gels in a Membraneless Diffusion Cell*, 280–283 (1989).

*Primary Examiner*—Thurman K. Page
*Assistant Examiner*—Kathryne E. Shelborne
*Attorney, Agent, or Firm*—Brown, Martin, Haller & McClain, LLP

[57] ABSTRACT

Topically applied compositions for transdermal administration of efficacious paid relief medication are described. The compositions contain several physiologically active components which act synergistically to attack pain-causing aspects of an injury or disorder while simultaneously blocking the immediate transmission and sensation of the pain. As the source of the pain is progressively diminished, the patient is spared the sensation of current and transient pain. Thus the compositions provide the patient with relief of both systemic and perceived pain. The compositions include medically effective amounts of a vasodilator, a non-steroidal anti-inflammatory drug, a membrane stabilizer, and a seratogenic reuptake inhibitor, and a medically acceptable carrier into which the foregoing are incorporated. Medically effective amounts of a topical anesthetic and/or a steroid anti-inflammatory drug are also advantageously included. A method of relief of a patient's pain which comprises topical administration to the patient of such compositions is also described.

53 Claims, No Drawings

MULTICOMPONENT PAIN RELIEF TOPICAL MEDICATION

BACKGROUND OF THE INVENTION

1. Field of the Invention

The invention herein relates to medications for relief of pain and inflammation associated with the production of pain. More particularly it relates to such pain and inflammation relief medication compositions which are administered topically.

2. Description of the Prior Art

Pain relief is a major focus of current medical attention. It is well established that patients respond much better to treatment for a wide variety of serious physical and neurological injuries and disorders if the pain associated with those conditions can be relieved. Similarly, even for relatively lesser injuries or disorders, where a physician's attention may be required only initially or at infrequent intervals while the patient recovers, the patient who can self-administer medication to relieve pain associated with the condition will recover faster, and during the recovery period will be able to resume normal activities earlier than if he or she was also simultaneously trying to cope with persistent pain.

Pain relief may be accomplished in two different ways. In one, the pain itself continues but is masked from the patient. This is essentially the function of the various types of anesthetics. The anesthetics do not attack the root cause of the pain, but rather block pain transmission so that the patient does not sense pain. Because they merely block pain sensation, anesthetics must be continually administered as long as the underlying condition causing the pain persists, or at least until the condition has improved to the point where the pain generated by the condition has decreased to a level that the patient can tolerate and resume daily functional activities and participate in kinematic functional activities.

More effective are treatment methods intended to attack the condition which is causing the pain. In most cases, once the physiological and neurotransmitter etiology of the pain begins to be alleviated, the sensation of pain is reduced.

There are, of course, a wide variety of ways to administer physiologically active agents. Probably the least objectionable to most patients is administration transdermally. A composition is applied to the outer surface of the skin and the active ingredients in the topical cream migrate from the cream through the skin and proceed to the site of the wound or affected organ. Many literature and patent references exist showing different types of topical creams, and great attention has been paid to various types of compounds or compositions to enhance the rate and completeness of such transdermal transfer of the active materials. While some of these references have described analgesics in general terms as among the physiologically active materials which can be administered transdermally, focus has been on the mechanism and rate of transdermal administration based on the using the specific compounds or classes of compounds identified in the references as the transdermal transmission rate "enhancers." Little or no attention has be directed toward effecting significant or comprehensive pain relief and migration of inflammation through transdermal administration of topically applied compositions.

SUMMARY OF THE INVENTION

I have now developed a unique class of compositions which are highly effective for the relief of a patient's pain and inflammation when applied topically. The compositions contain several physiologically active components which are administered to the patient transdermally and which act in combination to eliminate pain- and inflammation-causing aspects of an injury or disorder while simultaneously blocking the immediate transmission and sensation of the pain and the associated inflammation. As the source of the pain is progressively diminished, the patient is spared the sensation of current intransigent pain, with mitigation of the inflammatory pathways known to induce ascending pain patterns and propagation of ascending pain pathways. Thus the compositions provide the patient with relief of both systemic and perceived pain and the associated inflammation.

For brevity and ease of reading, the disclosure of the invention herein will sometimes refer simply to "pain" as the condition to which the patient is subject, rather than to "pain and associated inflammation" or "inflammation and associated pain." It will be understood, however, that the patient's pain is commonly, and in fact usually, associated with and resulting from inflamation at the site of the dysfunction, trauma, chronic disease or the like. Therefore, where the context is appropriate herein, the term "pain" should not be considered limiting but should be understood to include the associated inflammation and its effects. In this regard it will also be noted that the compositions of this invention not only are effective analgesics but also have significant anti-inflammatory properties.

While in the prior art some of the components of my composition have been described individually or occasionally in pairs for transdermal application, no one has heretofore developed a medication having the synergistic combination of the several critical components of the compositions described herein, which can be applied topically as a cream, paste or in similar form and which acts to alleviate pain in the comprehensive manner of the present invention. The overall combination claimed herein has not previously been described in the prior art nor has the prior art suggested such a combination, since as noted focus in the prior art has been on the materials which are identified as enhancing the rate of transdermal administration, rather than on the function or efficacy of the physiologically active materials thus administered. Where pain relief has been mentioned, it has been by reference to use of common anesthetics for masking pain to provide superficial and temporary relief. The present invention, however, overcomes all of the limitations of the prior materials and provides novel compositions which effectively and rapidly serve to alleviate current perceived pain while simultaneously systemically attacking pain generation at the source.

Therefore, in a broad embodiment, the present invention is of a pain relief composition for topical administration to a patient, comprising medically effective amounts of a vasodilator, a non-steroidal anti-inflammatory drug, a membrane stabilizer, and a seratogenic and nonadrenergic reuptake inhibitor, and additionally a medically acceptable carrier into which the foregoing are incorporated. Preferably the composition will be in the form of a body of viscous consistency having a viscosity sufficient to be retained in place on a patient's skin following administration while yet permitting effective and rapid diffusion of the medically active components thereof from the composition to the patient's skin surface and transdermal administration and delivery to the patient of the medically active components thereof.

In other embodiments the composition will also include medically effective amounts of a topical anesthetic, such as lidocaine, and/or a steroid anti-inflammatory drug, such as a corticosteroid.

In yet another broad embodiment, the invention is of a method for relief of a patient's pain which comprises topical administration to the patient of a composition comprising medically effective amounts of a vasodilator, a non-steroidal anti-inflammatory drug, a membrane stabilizer, and a seratogenic reuptake inhibitor, and additionally a medically acceptable carrier into which the foregoing are incorporated. Preferably administration comprises forming the composition as a body of viscous consistency having a viscosity sufficient to be retained in place on a patient's skin and thereafter causing effective and rapid diffusion of the medically active components thereof from the composition to the patient's skin surface and transdermal administration to the patient of the medically active components of the composition.

In yet other embodiments the method comprises administration of a composition which also includes medically effective amounts of a topical anesthetic, such as lidocaine, and/or a steroid anti-inflammatory drug, such as a corticosteroid.

DETAILED DESCRIPTION AND PREFERRED EMBODIMENTS

In the description below, each of the necessary and optional components will be described by its type, with a number of typical examples given and by the description of its nominal function. It will be, of course, understood that there are many studies which have been done regarding the mechanism of action of various medications and other physiologically active agents. However, notwithstanding extensive research, in many cases the actual mechanism of a compound or composition's function remain less than fully understood. Also, when there are combinations of two or more compounds or compositions, the operative mechanism of the combination is often different than the operative mechanisms of the individual components considered or administered separately. In addition, it is also widely recognized that individual patients can and do vary substantially in the reactions of their bodies to the administration of individual compounds or mixtures of compounds. It will therefore be understood that the discussion of the mechanisms in this specification are provided only to assist the reader in understanding the overall nature of the claimed compositions, and that the mechanisms described are postulated only and are not intended to be limiting to the scope of the claimed invention. It will also be understood by those skilled in the art that there may be alternative mechanisms involved and which predominate over or are in place of the described mechanisms, or that the mechanisms described herein may have additional aspects not discussed or may be applicable only under certain conditions or with certain patients. Considering the invention, therefore, one should focus on the chemical identity of the different components mentioned rather than on the function attributed to them for descriptive and exemplary purposes.

The first component of the composition will be a vasodilating agent. It is believed that this component induces both veno and arterial dilation, thus enhancing the absorption of the components of the composition. Typical examples of vasodilating agents which may be used include nitroglycerin, erythritol tetranitrate, isosorbide dinitrate, mannitol hexanitrate, pentaerythritol tetranitrate, papaverine, dipyridanaole and nifedipine, of which nitroglycerin is particularly preferred. The vasodilating agent will be present in the composition in an amount of 0.5% to 25%, preferably 0.5% to 5.0%, and most preferably approximately 2% (all percents herein are by weight, unless otherwise noted).

The second component is a non-steroidal anti-inflammatory agent or drug (NSAID). This component is directed toward alleviating and reducing pain mediated by prostoglandins at its source. Typical of the types of tissue illnesses and injuries to which these compositions are applicable include, but are not limited to, conditions of tenosynovitis, myositis, inflammatory pain associated with muscle, tendon and ligament sprains and strains, and autoimmune diseases such as arthritis. Typical of the non-steroidal anti-inflammatory agents which may be used are diclodenac, diflunisal, fenoprofen, flurbiprofen, ibuprofen, indomethacin, ketoprofen, melcofenamate, mefenamic acid, naproxen, phenylbutazone, piroxicam, sulindac, tiaprofenic acid, alcolfenac, desoxysulindac, aspirin, salicylamide, salicyclic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole neocinchophen, nimazole, proxazole citrate, tesicam, tesimide, tramadol, triflumidate or tolmetin, of which ketoprofen is a preferred component. The non-steroidal anti-inflammatory agent will be present in the composition in an amount of approximately 2% to 50%, preferably 2% to 12%, and more preferably on the order of about 10%.

The third component will be a membrane stabilizing agent. This component is believed to function to stabilize both sensory and motor axonal potentials. This then reduces the threshold for both sensory and motor axons to propagate an action potential and communicate an ascending or descending pain or motor function respectively. It is known that a principal source of pain from a disease or injury can be a destabilized nervous system. While the sensory component of the nervous system transmits pain impulses generated at the disease or wound site via ascending pain pathways, the instability of the sensory or motor nervous system at the site of disease and/or injury can lead to increased propagation and depolarization particularly of ascending pain pathways. It is will known that a high frequency of destabilization and depolarization of ascending nociceptive pathways will lead to increased cerebral perception of pain. Thus stabilizing the sensory and motor system and decreasing the instability and depolarization potential of the nervous system will decrease the ascending pain pathways and therefore decrease the frequency of depolarization of the ascending pain pathways and mitigate the cerebral perception of pain. This is a significant element in the overall reduction of a patient's pain level. A principal class of the membrane stabilizing agents which provide this function consists of carbamazepine and its analogs. The membrane stabilizing agent will be present in an amount of about 0.5% to 50%, preferably 0.5% to 5%, and more preferably approximately 2%.

The fourth ingredient required for the composition will be a seratogenic and nonadrenergic reuptake inhibitor. These compounds serve to block the pain pathways in the nervous system and therefore provide an anesthetic effect. While they do not primarily deal with the underlying pain generating condition, they do provide relief to the patient in a masking manner since they prevent the pain generation signals from the wound or diseased area from reaching the portion of the brain which would recognize those signals as being associated with pain and would manifest those signals as sensory pain felt by the patient. Typical examples of the seratogenic reuptake inhibitors include amitriptyline, amoxapine, clomipramine, desipramine, doxepin, imipramine, nortriptyline, protriptyline, isocarboxazid, phenelzine, tranylcypromine, maprotiline, trazodone or trimipriamine, of which amitriptyline is preferred. The seratogenic reuptake inhibitors will be present in the composition as 0.5% to 50%, preferably 0.5% to 10%, and more preferably approximately 2%.

In addition to the above described principal components, the compositions of this invention may also advantageously contain either or both a topical anesthetic and a anti-inflammatory steroid. The topical anesthetics operate as their name implies, in that they create a masking effect by desensitizing and blocking pain pathways at the skin level so that the pain sensations do not ultimately become manifest to the patient. Typical of the topical anesthetics are benzocaine, butamben, dibucaine, lidocaine, propoxycaine, procaine, mepivacaine, bupivacaine, pramoxine or tetracaine, or salts thereof, or mixtures thereof with menthol, of which lidocaine is preferred. The topical anesthetic will be present as from 0.5% to 25%, preferably 0.5% to 5%, and more preferably approximately 2% of the composition.

The anti-inflammatory steroid is preferably any of a number of typical well known corticosteroids including alcometasone, clocortolone, dexamethasone, hydrocortisone, hydrocortisone 21-acetate, prednisone, hydrocortisone 17-valerate, hydrocortisone 17-butyrate, betamethasone valerate, triamcinolone acetonide, flucinonide, desonide, flucinolone acetonide, dexamethasone, dexamethasone 21-phosphate, prednisolone, prednisolone 21-phosphate, haloprednone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone, flumethasone pivalate, flunisolide acetate, flucortolone, fluorometholone, fluperolone acetate, fluprednisolone, fluprednisolone valerate, meprednisone, methyl prednisolone, paramethasone acetate, prednisolamate, prednival, triamcinolone, triamcinolone hexacetonide, cortivazol, formocortal, nivazol or methylprednisone, of which hydrocortisone is preferred. The steroidal anti-inflammatory compound will be present in an amount from 0.5% to 25%, preferably 0.5% to 4%, and more preferably, approximately 2% of the composition. A steroidal anti-inflammatory agent is known to work in a different manner as compared to a non-steroidal anti-inflammatory medications described above, in that the former act through protein synthesis from DNA while the latter act by inhibiting prostaglandins. In the present compositions, therefore, the two represent a different type of components even though the result of their different actions result in a generally similar effect on the patient.

The various components will be mixed together and suspended in a suitable carrier, so that the final preparation will be in the form of a body of viscous consistency having a viscosity sufficient to be retained in place on a patient's skin following administration while yet permitting effective and rapid diffusion of the medically active components of the composition from within the preparation body to the patient's skin surface for transdermal administration of the medically active components to the patient. Typical of the forms which the preparation body may take are gels, ointments or creams.

These preparations can be either aqueous or organic based, using pharmaceutically acceptable carriers. The choice of carrier will depend on compatibility with the particular individual components used in the preparations. A stabilizing system, intended for maintaining the chemical integrity of the anti-inflammatory agents, may also be included if warranted. The carrier may be one or a plurality of compounds suitable for topical administration, and may be water (preferably deionized), mineral oil, a lower alcohol (e.g., ethanol, isopropanol), a mono- or polyglycol (e.g., ethylene glycol, propylene glycol; polyethylene glycol; polyoxyalkylene derivatives of propylene glycol), a fatty acid ester (e.g., any of the well known alkyl stearates, oleates and linoleates) or other organic compounds or polymers such as dimethylsulfoxide, dimethylformamide, dimethylacetamide, 1,2,6-hexanetriol, butanediol and other liquid solvents completely or partially miscible with water. One may also include anti-oxidants (e.g., butylated hydroxytoluene, butylated hydroxyanisole or propyl gallate), perfumes, colorants, and other conventional additives which are known to be effective and suitable for topical application. It will of course be evident that any and all additives must be compatible with the active components of the preparation and the carrier. A particularly preferred family of carriers is the group of nonionic polyalkylene derivatives of propylene glycol sold under the trademark "Pluronic" from Wyandotte Chemicals Corp. These polyglycols have molecular weights in the range of 1,000 to >15,000 and are available in solid or liquid forms, and can be mixed with each other or combined with water or organic liquids so that those skilled in the art can readily obtain the degree of viscosity desired for any of the products of this invention.

Control of the degree of viscosity can also be accomplished by the use of gelling agents such as hydroxypropyl cellulose, hydroxyethyl cellulose, carbonaceous polymers, and combinations thereof. Generally the gelling agent is added to the mixture of active components and carrier with agitation, while avoiding clumping or excess air entrapment, using a glass-lined or stainless steel container.

One forms the preparation in an ointment, cream or paste form (water immiscible or water miscible) by heating white petrolatum in a suitable container (glass-lined or stainless steel) until fluid and adding the active ingredients in the form of a suspension, a finely powdered, micronized state, or solubilized in a suitable solvent system. Suitable oil soluble surfactants (e.g., hydroxylated lanolin, ethoxylated lanolin derivatives or polyoxyethylene esters) can be added to the petrolatum to make the preparation water miscible, or the surfactants may be omitted to make the ointment water-immiscible. The method of preparation of dissolve the solid ingredients in the primary carrier using a suitable container (glass or stainless steel lined) and mixers, with filtration and viscosity adjustment as necessary, is well known.

The transdermal flux rate of the composition, as well as the optimal amount of carrier to be used, will vary depending on the carrier selected. Given the disclosure herein, those skilled in the art will be able to select the optimal carrier and optimal weight ratio of carrier to components for the desired application. The carrier must be selected such that the rate of transport of the medically active components through the skin is sufficiently high that a pharmaceutically effective concentration of each component can be achieved with a skin contact area of reasonable size within a reasonable time. In general, the maximum area of skin contact that is practical for a single application should be no greater than 20 or 25 cm$^2$, and preferably less than 6 cm$^2$. In a modification of the invention, two or more skin application sites can be used simultaneously on separate skin areas.

The carrier (solvent) will be present in a sufficient amount to make up the balance of 100% of the composition. It will be noted above that the various concentrations mentioned can, in some combinations, appear to add to more than 100%. It will, of course, be recognized by those skilled in the art that such combinations are outside the scope of this invention. Where one or two components are taken in relatively large concentrations, the concentrations of the remaining components will be lessened appropriately to keep the overall total concentration of each component, including the carrier, to an amount such that the total will equal 100%. Alternatively, one can describe the concentration in terms of parts by weight, with the total number of parts in the composition being the sum of all of the components taken in the weight quantities desired by the formulator. Concentrations of components described by parts do not necessarily add to a total of 100 parts for the entire composition, but if the desired total number of parts in the composition is set at 100, then parts by weight and percent by weight for the concentration of the individual ingredients will be equal.

The administration this product will be apparent from the above description and its physical nature. The desired amount of the composition is merely applied to a particular area of the patient's skin and allowed to penetrate, which will require only a relatively short amount of time. The preparation may be applied directly from a supply in a small container, such as a cream jar, or may be incorporated into a dressing or patch which is placed on the patient's skin. Direct use of the preparation is preferred, however, since it has been well established that diffusion of active materials out of a dressing or patch may be slow and is often incomplete. By direct application, however, the entire amount of the active ingredients can be transmitted into the patient transdermally more effectively. If desired for cleanliness or to keep portions of the cream or solution from getting on or staining the patient's clothing, however, a sterile dressing can be placed over the applied cream to separate it and protect it from the environment or adjacent clothing while it is absorbed through the skin.

The number of applications of the composition, the frequency of such applications, and the quantity to be administered with each application, will be determined by the physician in most cases. The patient can then be instructed as to how to measure the appropriate amount and how to ensure that the appropriate schedule for administration is maintained.

It will of course be understood that selection of the particular compounds representing each of the required and/or optional components will be chosen such that they are mutually compatible and also compatible with the carrier. While not all interactions of the various drugs are fully known or are completely predictable, those skilled in the art will have no difficulty determining compatibility by many of the conventional techniques known and widely described in literature, if any incompatibility is suspected or anticipated for a particular combination of specific components.

It is contemplated that the compositions of this invention will provide significant relief to patients with all types of acute inflammatory injuries. These would include, but not be limited to, muscle, ligament, tendon and myoligamentous strains and sprains; overuse syndromes which have acute inflammatory actions such an tenosynovitis and peripheral neuritis; conditions as mentioned and others resulting from sports injuries and industrial injuries, such as fibromyalgia and myofascial pain syndromes; chronic pain syndromes such as osteoarthritis of the ankles, knees, elbows, shoulders and hips; and low back strains characterized by both soft tissue injuries and osteoarthritis of the facet joints or of the spinal structure. Experimental use to date with some 300 patients have indicated that application of various compositions of this invention two or three times a day topically to the skin area particular to the pain and inflammation results in a significant reduction of the perception of pain in approximately 75% of the cases.

It will be evident that there are numerous embodiments of the present invention which, while not expressly described above, are clearly within the scope and spirit of the invention. The above description is therefore intended to be exemplary only and the scope of the invention is to be determined solely by the appended claims.

I claim:

1. A pain relief composition for topical administration to a patient, comprising medically effective amounts of a vasodilator, a non-steroidal anti-inflammatory drug, a membrane stabilizer, and a seratogenic and nonadrenergic reuptake inhibitor, and additionally a medically acceptable carrier into which the foregoing are incorporated.

2. A composition as in claim 1 wherein said vasodilator comprises a systemic nitrate compound.

3. A composition as in claim 2 wherein said vasodilator comprises nitroglycerin, erythrityl tetranitrate, isosorbide dinitrate or pentaerythritol tetranitrate.

4. A composition as in claim 3 wherein said vasodilator comprises nitroglycerin.

5. A composition as in claim 1 wherein said non-steroidal anti-inflammatory drug produces an analgesic effect.

6. A composition as in claim 5 wherein said non-steroidal anti-inflammatory analgesic comprises diclodenac, diflunisal, fenoprofen, flurbiprofen, ibuprofen, indomethacin, ketoprofen, melcofenamate, mefenamic acid, naproxen, phenylbutazone, piroxicam, sulindac, tiaprofenic acid or tolmetin.

7. A composition as in claim 6 wherein said non-steroidal anti-inflammatory analgesic comprises ketoprofen.

8. A composition as in claim 1 wherein said membrane stabilizer comprises carbamazepine.

9. A composition as in claim 8 wherein said seratogenic reuptake inhibitor comprises an antidepressant.

10. A composition as in claim 9 wherein said seratogenic reuptake inhibitor comprises amitriptyline, amoxapine, clomipramine, desipramine, doxepin, imipramine, nortriptyline, protriptyline or trimipriamine.

11. A composition as in claim 10 wherein said seratogenic reuptake inhibitor comprises amitriptyline.

12. A composition as in claim 1 further comprising medically effective amounts of a topical anesthetic, also incorporated into said carrier.

13. A composition as in claim 12 wherein said topical anesthetic comprises benzocaine, butamben, dibucaine, lidocaine, pramoxine or tetracaine, or mixtures thereof with menthol.

14. A composition as in claim 13 wherein said topical anesthetic comprises lidocaine.

15. A composition as in claim 1 further comprising medically effective amounts of a steroid anti-inflammatory drug, also incorporated into said carrier.

16. A composition as in claim 15 wherein said steroid anti-inflammatory drug comprises a corticosteroid.

17. A composition as in claim 16 wherein said steroid anti-inflammatory drug comprises alcometasone, clocortolone, dexamethasone, hydrocortisone, hydrocortisone acetate or methylprednisone.

18. A composition as in claim 17 wherein said steroid anti-inflammatory drug comprises hydrocortisone.

19. A composition as in claim 1 comprising about 0.5–25 parts of said vasodilator, about 2–50 parts of said non-steroidal anti-inflammatory drug, about 5–50 parts of said membrane stabilizer, about 0.5–50 parts of said seratogenic reuptake inhibitor, and the balance being sufficient parts of said carrier into which the foregoing are incorporated to form said topically applicable creme.

20. A composition as in claim 19 wherein said vasodilator is present as about 0.5–5 parts.

21. A composition as in claim 20 wherein said vasodilator is present as about 2 parts.

22. A composition as in claim 19 wherein said non-steroid anti-inflammatory drug is present as about 2–12 parts.

23. A composition as in claim 22 wherein said non-steroid anti-inflammatory drug is present as about 10 parts.

24. A composition as in claim 19 wherein said membrane stabilizer is present as about 0.5–5 parts.

25. A composition as in claim 24 wherein said membrane stabilizer is present as about 2 parts.

26. A composition as in claim 19 wherein said seratogenic reuptake inhibitor stabilizer is present as about 0.5–10 parts.

27. A composition as in claim 26 wherein said seratogenic reuptake inhibitor is present as about 2 parts.

28. A composition as in claim 19 further comprising about 0.5–25 parts of a topical anesthetic, also incorporated into said carrier.

29. A composition as in claim 19 wherein said topical anesthetic is present as about 0.5–5 parts.

30. A composition as in claim 29 wherein said topical anesthetic is present as about 2 parts.

31. A composition as in claim 19 further comprising medically effective amounts of a steroid anti-inflammatory drug, also incorporated into said carrier.

32. A composition as in claim 31 wherein said steroid anti-inflammatory drug is present as about 0.5–4 parts.

33. A composition as in claim 32 wherein said steroid anti-inflammatory drug is present as about 2 parts.

34. A composition as in claim 1 comprising medically effective amounts of nitroglycerin, ketoprofen, carbamazepine and amitriptyline, and additionally a medically acceptable carrier into which the foregoing are incorporated, said composition being in the form of a topically applicable creme.

35. A composition as in claim 34 further comprising medically effective amounts of a lidocaine, also incorporated into said carrier.

36. A composition as in claim 34 further comprising medically effective amounts of hydrocortisone, also incorporated into said carrier.

37. A composition as in claim 34 comprising about 0.5–25 parts of nitroglycerin, about 2–50 parts of ketoprofen, about 5–50 parts of carbamazepine, about 0.5–50 parts of amitriptyline, and the balance being sufficient parts of said carrier into which the foregoing are incorporated to form said topically applicable creme.

38. A composition as in claim 37 further comprising about 0.5–25 parts of lidocaine, also incorporated into said carrier.

39. A composition as in claim 38 further comprising about 0.5–4 parts of hydrocortisone, also incorporated into said carrier.

40. A composition as in claim 1 wherein said composition is in the form of a body of viscous consistency having a viscosity sufficient to be retained in place on a patient's skin following administration while yet permitting effective and rapid diffusion of said medically active components thereof from said composition to the patient's skin surface for transdermal administration of said medically active components thereof.

41. A method for relief of a patient's pain which comprises topical administration to said patient of a composition comprising medically effective amounts of a vasodilator, a non-steroidal anti-inflammatory drug, a membrane stabilizer, and a seratogenic reuptake inhibitor, and additionally a medically acceptable carrier into which the foregoing are incorporated.

42. A method as in claim 41 wherein said composition comprises about 0.5–25 parts of said vasodilator, about 2–50 parts of said non-steroidal anti-inflammatory drug, about 5–50 parts of said membrane stabilizer, about 0.5–50 parts of said seratogenic reuptake inhibitor, and the balance being sufficient parts of said carrier into which the foregoing are incorporated to form said topically applicable creme.

43. A method as in claim 41 wherein said composition further comprises medically effective amounts of a topical anesthetic, also incorporated into said carrier.

44. A method as in claim 43 wherein said topical anesthetic is present as about 0.5–25 parts of said composition.

45. A method as in claim 41 wherein said composition further comprises medically effective amounts of a steroid anti-inflammatory drug, also incorporated into said carrier.

46. A method as in claim 45 wherein said steroid anti-inflammatory drug is present as about 0.5–25 parts of said composition.

47. A method as in claim 41 which comprises topical administration to said patient of a composition comprising medically effective amounts of nitroglycerin, ketoprofen, carbamazepine and amitriptyline, and additionally a medically acceptable carrier into which the foregoing are incorporated, said composition being in the form of a topically applicable creme.

48. A method as in claim 47 wherein said composition comprises about 0.5–25 parts of nitroglycerin, about 2–50 parts of ketoprofen, about 5–50 parts of carbamazepine, and about 0.5–50 parts of amitriptyline, and the balance being sufficient parts of said carrier into which the foregoing are incorporated to form said topically applicable creme.

49. A method as in claim 47 wherein said composition further comprises medically effective amounts of lidocaine, also incorporated into said carrier.

50. A method as in claim 49 wherein said lidocaine is present as about 0.5–25 parts of said composition.

51. A method as in claim 47 wherein said composition further comprises medically effective amounts of hydrocortisone, also incorporated into said carrier.

52. A method as in claim 51 wherein said hydrocortisone is present as about 0.5–25 parts of said composition.

53. A method as in claim 41 wherein said administration comprises forming said composition as a body of viscous consistency having a viscosity sufficient to be retained in place on a patient's skin and thereafter causing effective and rapid diffusion of said medically active components thereof from said composition to the patient's skin surface and transdermal administration to said patient of said medically active components of said composition.

* * * * *